United States Patent
Painter et al.

(10) Patent No.: US 10,370,321 B2
(45) Date of Patent: Aug. 6, 2019

(54) ACETIC ACID RECOVERY FROM WOOD ACETYLATION

(71) Applicant: Tricoya Technologies Ltd, London (GB)

(72) Inventors: Benjamin Thomas Painter, London (GB); Stephen John Benstead, London (GB)

(73) Assignee: Tricoya Technologies Ltd., London (GB)

( * ) Notice: Subject to any disclaimer, the term of this patent is extended or adjusted under 35 U.S.C. 154(b) by 85 days.

(21) Appl. No.: 15/326,675

(22) PCT Filed: Jul. 17, 2015

(86) PCT No.: PCT/EP2015/066433
§ 371 (c)(1),
(2) Date: Jan. 17, 2017

(87) PCT Pub. No.: WO2016/009051
PCT Pub. Date: Jan. 21, 2016

(65) Prior Publication Data
US 2017/0204042 A1     Jul. 20, 2017

(30) Foreign Application Priority Data

Jul. 18, 2014    (EP) .................................. 14177679.9

(51) Int. Cl.
| | |
|---|---|
| C07C 51/46 | (2006.01) |
| B01J 19/24 | (2006.01) |
| B01D 3/14 | (2006.01) |
| C08B 3/06 | (2006.01) |
| C07C 51/44 | (2006.01) |

(Continued)

(52) U.S. Cl.
CPC ................ *C07C 51/46* (2013.01); *B01D 3/14* (2013.01); *B01J 19/245* (2013.01); *C07C 51/44* (2013.01); *C07C 51/56* (2013.01); *C08B 3/06* (2013.01); *C08H 8/00* (2013.01); *B01J 2219/24* (2013.01); *B27K 3/346* (2013.01); *Y02E 50/14* (2013.01)

(58) Field of Classification Search
CPC ......... C07C 51/44; C07C 51/46; C07C 51/56; B01D 3/14; C08H 8/00; B01J 19/245; C08B 3/06; B27K 3/346
See application file for complete search history.

(56) References Cited

U.S. PATENT DOCUMENTS

| | | | |
|---|---|---|---|
| 2004/0258941 A1* | 12/2004 | Neogi | .................. C08B 3/00 428/537.1 |
| 2009/0234157 A1 | 9/2009 | Warner et al. | |
| 2014/0066653 A1* | 3/2014 | Warner | .................. C07C 51/573 562/892 |

FOREIGN PATENT DOCUMENTS

WO    2009120257    10/2009

OTHER PUBLICATIONS

Richardson, J.F. et al. (2002) Particle Technology & Separation Processes, 5th edition, vol. 2, Elsevier, 1229 pgs [Office action cites p. 656].*

* cited by examiner

*Primary Examiner* — Brian A McCaig
(74) *Attorney, Agent, or Firm* — OspreyIP, pllc; James R. Cartiglia

(57) ABSTRACT

Disclosed is the integration of the production of acetic anhydride from ketene, and the acetylation of wood using acetylation fluid comprising acetic acid and acetic anhydride. The invention involves combining acetic acid obtained from distillation of acetylation fluid with a residual (Continued)

aqueous acetic acid stream as obtained from ketene production.

15 Claims, 4 Drawing Sheets

(51) Int. Cl.
*C07C 51/56* (2006.01)
*C08H 8/00* (2010.01)
*B27K 3/34* (2006.01)

ACETIC ACID RECOVERY FROM WOOD ACETYLATION

FIELD OF THE INVENTION

The invention pertains to a process for the purification of acetic acid recovered from a wood acetylation process. Particularly, the invention pertains to a process for the integration of the acetylation of wood and the production of acetic anhydride from acetic acid, and an integrated plant.

BACKGROUND OF THE INVENTION

A well-known process for the production of acetic anhydride from acetic acid involves the formation of ketene (ethenone). Thereby ketene is produced by dehydrating acetic acid at high temperatures (typically in a ketene furnace operated at temperatures of the order of 700° C. to 750° C.). Subsequently, the ketene is reacted with acetic acid in an exothermic reaction leading to the formation of acetic anhydride.

Interestingly, both acetic acid and acetic anhydride are used in processes for the acetylation of wood. These processes, for which there is an increasing demand, serve to provide the wood with improved material properties, e.g. dimensional stability, hardness, durability, etc. In these processes, excess acetylation medium, typically a mixture of acetic anhydride and acetic acid, is ultimately removed from the wood. It is thereby desired to avoid wasting the removed acetylation medium, and preferably to recirculate and re-use it in wood acetylation.

Suitable techniques exist for recovering acetic anhydride, by separating it from acetic acid, after which the acetic anhydride can be re-used in wood acetylation. The acetic acid, however, comes in an excess ratio after wood acetylation as it is formed as a byproduct thereof, and it would be desired to put this to separate use, sell it as a chemical, and/or use it in the production of ketene. However, the specific source of the acetic acid, viz. from the acetylation of wood, comes with inherent limitations to their further use due to the presence impurities such as that of terpenes and terpenoid impurities from the wood. Particularly terpenes and terpenoids are difficult to remove. This limits the use of acetic acid as recovered from wood acetylation. E.g., using it in a ketene furnace is not desired, as the aforementioned impurities are prone to result in coke formation in the furnace, as a result of the high temperatures applied therein.

The foregoing issue is addressed in WO 2009/120257, by azeotropic distillation, wherein acetic acid comprising the aforementioned impurities is supplied to a distillation column together with water. Whilst the reference thus teaches a method of obtaining purified acetic acid from wood acetylation, it does not relate to the production of acetic anhydride and, particularly, it does not teach how to effectively integrate the production of acetic anhydride and the acetylation of wood. Also, the addition of water to the distillation column reduces the economic feasibility of the process.

It is desired to provide a method by which the acetylation of wood and the production of acetic anhydride can be effectively integrated. Also, it is desired to thereby make optimal use of sources of liquid as available from wood acetylation.

SUMMARY OF THE INVENTION

In order to better address one or more of the foregoing desires, the invention, in one aspect, concerns a process for the purification of acetic acid recovered from a wood acetylation process, wherein wood acetylation fluid obtained from a wood acetylation process, said fluid comprising acetic acid and acetic anhydride, is subjected to acetic acid recovery (e.g. by distillation), and wherein acetic acid thereby recovered is mixed with a residual aqueous acetic acid stream from a unit for the production of ketene from acetic acid, and the resulting mixture is subjected to distillation so as to produce purified acetic acid.

In another aspect, the invention presents a system comprising a wood acetylation unit and a ketene production unit, said ketene production unit comprising a treatment section for the recovery of acetic acid from a residual aqueous acetic acid stream, the system comprising a separation unit for the separation of acetic acid obtained from the wood acetylation unit, said separation unit being in fluid communication with the treatment section, and wherein the treatment section comprises a distillation unit.

DETAILED DESCRIPTION OF THE INVENTION

Figure 1:
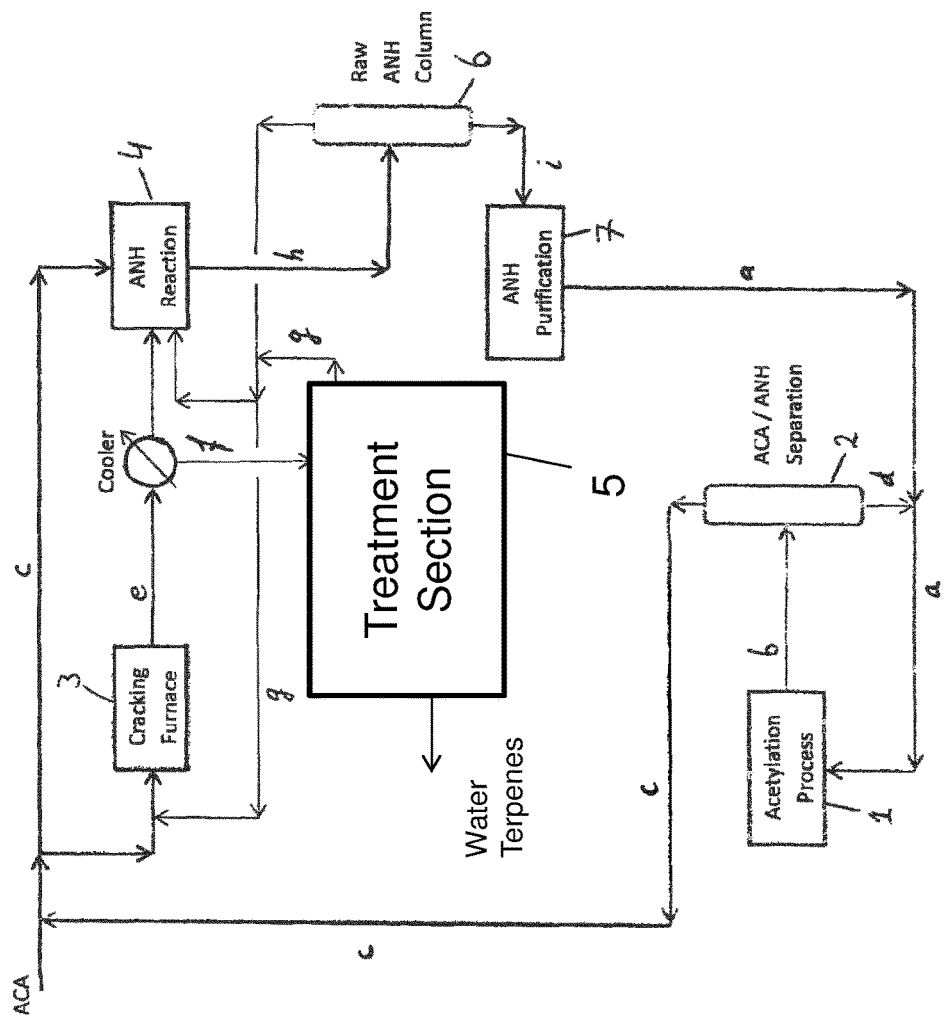
FIG. 1 shows a scheme for a ketene-based production unit integrated with a wood acetylation unit coupled without additional measures, not according to the invention.

In a broad sense, the invention is based on the judicious insight to make use of azeotropic distillation of terpenes in the integration of wood acetylation and acetic anhydride production. Accordingly, acetic acid is separated from recovered wood acetylation fluid, and sent to the section of a unit for the production of ketene from acetic acid, wherein residual aqueous acetic acid is treated so as to recover acetic acid. Since this is an aqueous stream, the treatment thereof by distillation will allow terpenes and/or terpenoids to be azeotropically removed.

The residual aqueous acetic acid stream results from the fact that, by definition, a unit for the production of ketene from acetic acid (such as a ketene furnace) will not yield a full conversion of acetic acid into ketene. I.e., from said unit at least two streams are obtained. One being a product stream, comprising the formed ketene, the other being said residual stream.

As a result of the invention, an integrated process is realized wherein wood can be subjected to acetylation, and recovered acetylation fluid is re-used. The recovery of the acetylation fluid, which fluid comprises a mixture of acetic acid and acetic anhydride, includes a step wherein said fluid is subjected to acetic acid recovery. Such recovery can generally be done by distillation, but other methods of separating acetic acid from acetic anhydride are suitable as well. This step results in the recovery of both acetic acid and acetic anhydride.

The thus recovered acetic anhydride can be separated and put to any desired use. In the invention, the recovered acetic anhydride is preferably recirculated to the feed stream of the acetylation fluid used in the wood acetylation process.

The recovered acetic acid, which will normally contain the aforementioned terpene and terpenoid impurities, is mixed with the residual aqueous acetic acid stream that is normally obtained, as a side-stream, in the production of ketene from acetic acid. The purified acetic acid thereby obtained, can be put to any use. Preferably, however, it is recirculated to a feed stream of acetic acid used in the production of ketene and/or in the production of acetic anhydride.

The ketene produced can be put to any use. However, in accordance with the invention it is preferred to provide an integrated process, wherein the formed ketene is subsequently used in a process for the production of acetic anhydride. The ketene is thereby reacted with acetic acid. As indicated above, the feed streams of acetic acid in either or both of the production of ketene and the subsequent production of acetic anhydride, may comprise purified acetic acid obtained from the residual aqueous acetic acid stream from the ketene production.

The acetic anhydride thereby produced can be put to any use. However, in accordance with the invention it is preferred to provide a fully integrated process, wherein the formed acetic anhydride is recirculated to the feed stream of acetylation fluid, used in a unit for the acetylation of wood, preferably the same unit from which the acetylation fluid is recovered as discussed in the foregoing embodiments.

Thus, in a preferred embodiment of the invention, an integrated process results wherein acetylation fluid recovered from wood acetylation is re-used in one or more process steps that ultimately lead back to the wood acetylation. The acetic anhydride separated from the recovered acetylation fluid is preferably recirculated directly to the acetylation fluid feed stream. The acetic acid separated from the recovered acetylation fluid is, after purification in accordance with the invention, ultimately used in the production of acetic anhydride, which acetic anhydride in turn is used in the acetylation fluid feed stream. Said use of acetic acid in the production of acetic anhydride is either directly, as a reactant in the synthesis of acetic anhydride from acetic acid and ketene, or indirectly, as a reactant in the preceding formation of ketene from acetic acid.

In an interesting embodiment, the invention makes judicious use of the possible situation that the output of the acetic anhydride production unit may require adjustment of the ratio of acetic anhydride to acetic acid, so as to become richer in acetic anhydride. This is related to the fact that a full conversion of acetic acid into acetic anhydride will usually not be achieved in practice. A unit for the separation of acetic acid and acetic anhydride (typically a distillation column, sometimes referred to as a "raw anhydride column") is employed in order to adjust the ratio of acetic anhydride to acetic acid in the product stream coming from the acetic anhydride production unit. The output of said separation unit will preferably be suitable as a wood acetylation fluid, such fluid preferably comprising acetic anhydride (ANH) and acetic acid (ACA) in a ratio ANH:ACA of from 80:20 to 100:0, preferably 90:10 to 95:5.

This adjustment (typically by distilling off acetic acid from the acetic anhydride produced) will thus result in a separate stream of acetic acid. It has now been recognized by the present inventors, that the integration of wood acetylation and acetic anhydride production, can be optimized in respect of equipment and operational costs. For, considering that the unit for the production of acetic anhydride will generally be followed by a section for the separation of acetic acid from acetic anhydride (e.g., by distillation), this same section can be used for the separation of acetic acid and acetic anhydride from the acetylation fluid as recovered from wood acetylation.

Thus, in this embodiment of the invention raw acetic anhydride is produced that is subjected to a concentration increase by separating acetic acid therefrom in a unit for the separation of acetic acid and acetic anhydride, and wherein the same separation unit is used for the recovery of acetic acid from the wood acetylation fluid.

The integration of wood acetylation and acetic anhydride production according to the invention can be carried out both in existing plants and in designing new plants. E.g., a new ketene-based production unit for acetic anhydride can be built next to an existing wood acetylation unit, and coupled to it in accordance with one or more embodiments of the invention. Also, a new wood acetylation unit can be built next to an existing ketene-based production unit for acetic anhydride. Or, in the event that a wood acetylation unit and a ketene-based acetic anhydride production unit already exist next to each other, these can become integrated. In the event that the units are already integrated in another way, the manner in which such plants are coupled can be changed so as to be in conformity with the invention as described hereinbefore.

The separation of recovered acetylation fluid into acetic acid and acetic anhydride according to the invention, can be of particular advantage in wood acetylation plants that, for other reasons, already contain a distillation unit for recovered acetylation fluid. In that event, the integration of such an existing wood acetylation unit with a ketene-based acetic anhydride production unit can be advantageously carried out by arranging the appropriate flow lines so as to have acetic acid retrieved in said distillation unit combined with the residual aqueous acetic acid stream from ketene production.

The equipments and technologies applied are well-known to the skilled person. This pertains to units for the acetylation of wood, such as wood acetylation reactors, and the customary ancillary equipment thereof, e.g. a filter section for removing wood residues from recovered acetylation fluid. Similarly, this pertains to separation units such as distillation units (e.g. distillation equipment such as a distillation column), to ketene production sections (typically a ketene furnace), acetic anhydride production sections (typically a reactor suitable for reacting ketene with acetic acid).

Wood acetylation units for use in the present invention can be those suitable for the acetylation of solid wood, such as wood beams or planks Said wood acetylation units can also be those suitable for the acetylation of wood elements such as flour, fibres, strands, or chips. The wood acetylation processes applied in the present invention thus are not limited to any size, shape, or species of wood. A great variety of such processes is well-known to the skilled person.

The invention also pertains to a system comprising a wood acetylation section and a ketene production unit, said ketene production unit comprising a treatment section for the recovery of acetic acid from a residual aqueous acetic acid stream, the system comprising a separation section for the separation of acetic acid obtained from the wood acetylation unit, said separation section being in fluid communication with said treatment section, and wherein said treatment section comprises a distillation unit. The latter serves to allow acetic acid recovered from wood acetylation, to be purified by having terpenes and/or terpenoids removed as a result of azeotropic distillation with water.

In an interesting embodiment of the foregoing system, the ketene production unit is comprised in a section for the production of acetic anhydride. Said section comprising the ketene production unit and, downstream thereof, an acetic anhydride production unit.

Preferably, the system of the invention comprises a wood acetylation section integrated with an acetic anhydride production section in the following manner. Therein said wood acetylation section comprises an inlet and an outlet for acetylation fluid, and said acetic anhydride production section comprises a unit for the production of ketene from acetic acid and, downstream thereof, a unit for the production of acetic anhydride from ketene and acetic acid. Said acetic anhydride production unit comprises an inlet for ketene, an inlet for acetic acid, and an outlet for acetic anhydride, and said ketene production unit comprises an inlet for acetic acid, an outlet for ketene. The outlet for ketene is in fluid communication (such as by a gas flow line) with the inlet for ketene of the acetic anhydride production unit. The ketene production unit comprises a separate outlet to a section for the treatment of residual aqueous acetic acid. According to the invention, the outlet for acetylation fluid of the wood acetylation section is in fluid communication with a section for the separation of acetic acid and acetic anhydride; an acetic acid outlet of said section is in fluid communication with an inlet of the section for the treatment of residual aqueous acetic acid. The latter section has an outlet for purified acetic acid, said outlet being in fluid communication with an inlet for acetic acid of the acetic anhydride production section. Said inlet can be an inlet to the ketene production unit, an inlet to the acetic anhydride production unit, or both.

In an embodiment of the system of the invention, an outlet for acetic anhydride of the acetic anhydride production unit, is in fluid communication with a section for the separation of acetic acid and acetic anhydride (such as a distillation unit). The latter separation section has an acetic anhydride outlet which can be in fluid communication with an inlet for acetylation fluid of the wood acetylation section. In an interesting embodiment, said separation section is also used as the section for the separation of acetic acid and acetic anhydride from the acetylation fluid recovered from the wood acetylation section. To this end, said separation section has an outlet for acetic acid that is in fluid communication with an inlet of the section for the treatment of residual aqueous acetic acid from the ketene production unit.

The invention will be further explained hereinafter with reference to the drawings. These drawings do not limit the invention. As the drawings may relate to specific embodiments of the invention, the skilled person will understand that the invention is more generally applicable, and the disclosure in the drawings is not limited to any specific designs or numbers given therein.

In the figures, the following elements are shown.
Equipment parts:
(1) Wood acetylation plant
(2) Acetic acid/acetic anhydride separation unit
(3) Ketene production unit
(4) Acetic anhydride production unit
(5) Treatment section for recovering residual aqueous acetic acid
(6) Acetic anhydride distillation unit
(7) Acetic anhydride purification unit
Process streams:
(a) Fresh acetylation fluid
(b) Acetylation fluid recovered from wood acetylation
(c) Acetic acid
(d) Acetic anhydride separated from acetic acid
(e) Ketene
(f) Residual aqueous acetic acid
(g) Acetic acid recovered
(h) Raw acetic anhydride (mixture with acetic acid)
(i) Enriched acetic anhydride (reduced acetic acid content)

FIG. 1 shows a scheme for a ketene-based acetic anhydride production plant (comprising a ketene production unit (3) and an acetic anhydride production unit (4) integrated with a wood acetylation plant (1). Herein the plants are coupled without any additional measures, i.e. not according to the invention. Acetylation fluid (stream a) is fed to a wood acetylation plant (1). Recovered acetylation fluid (b) is subjected to acetic acid separation in a first acetic acid/acetic anhydride separation unit (2), resulting in a stream (c) of acetic acid separated from acetic anhydride and a stream (d) of acetic anhydride separated from acetic acid. The stream (c) of acetic acid separated from acetic anhydride is sent to an acetic anhydride production section comprising a ketene production unit (3) and an acetic anhydride production unit (4). The ketene production unit (3) is connected to, downstream thereof, a treatment section (5) for recovering residual aqueous acetic acid (f). Acetic acid recovered therefrom (g) is sent to the ketene production unit (3) and/or the acetic anhydride production unit (4). Ketene produced (e) is sent to an acetic anhydride production unit (4). Raw anhydride produced (h) is sent to an acetic anhydride distillation unit (6). Acetic acid obtained therefrom (c) is sent to the acetic anhydride production section mentioned above. The enriched acetic anhydride (i), having a reduced acetic acid content, is sent to a purification unit (7) and purified acetylation fluid thereby obtained (i) is fed, as fresh acetylation fluid (a) to the wood acetylation section (1).

Figure 2:
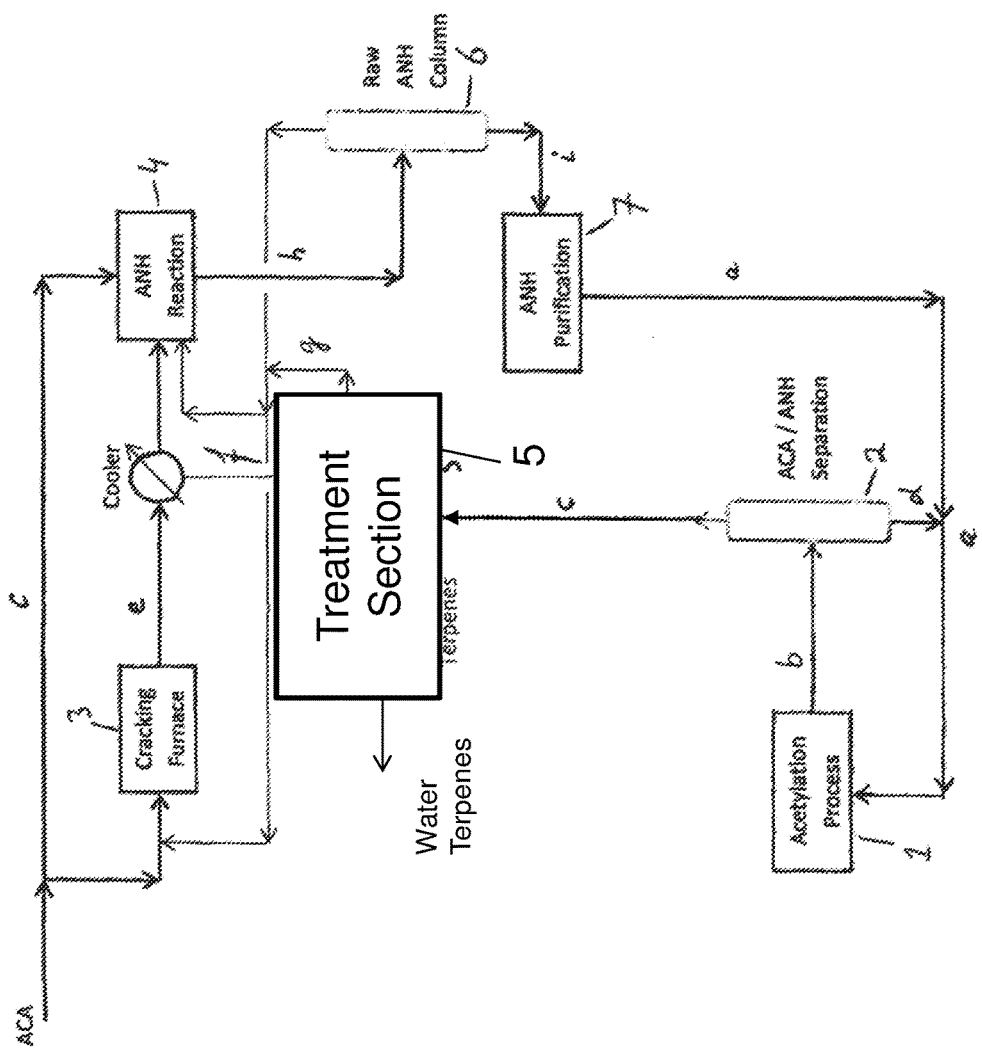
FIG. 2 shows a scheme for a ketene-based production unit integrated with a wood acetylation unit coupled according to an embodiment of the invention.

FIG. 2 shows a scheme for a ketene-based production plant integrated with a wood acetylation plant in accordance with an embodiment of the invention. Herein the stream (c) of acetic acid separated from acetic anhydride is sent to the treatment section (5) for recovering residual aqueous acetic acid.

Figure 3:
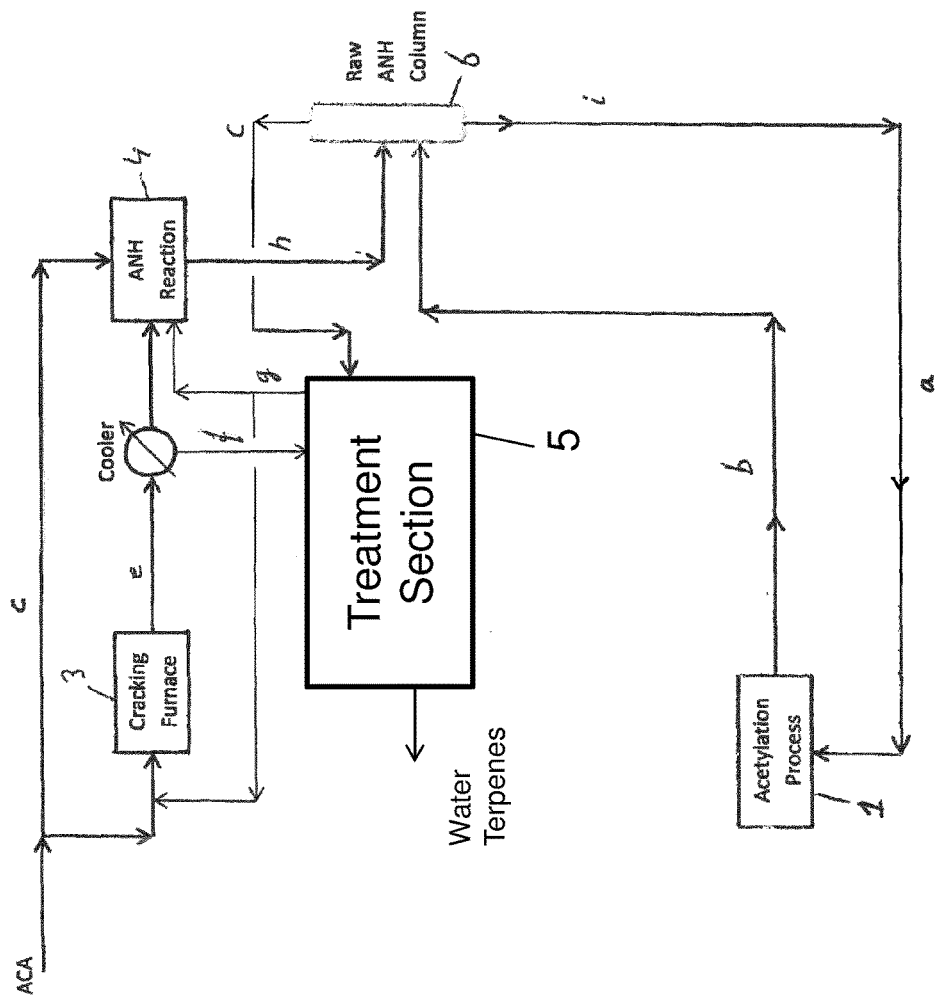
FIG. 3 shows a scheme as in FIG. 2, according to another embodiment of the invention.
Figure 4:
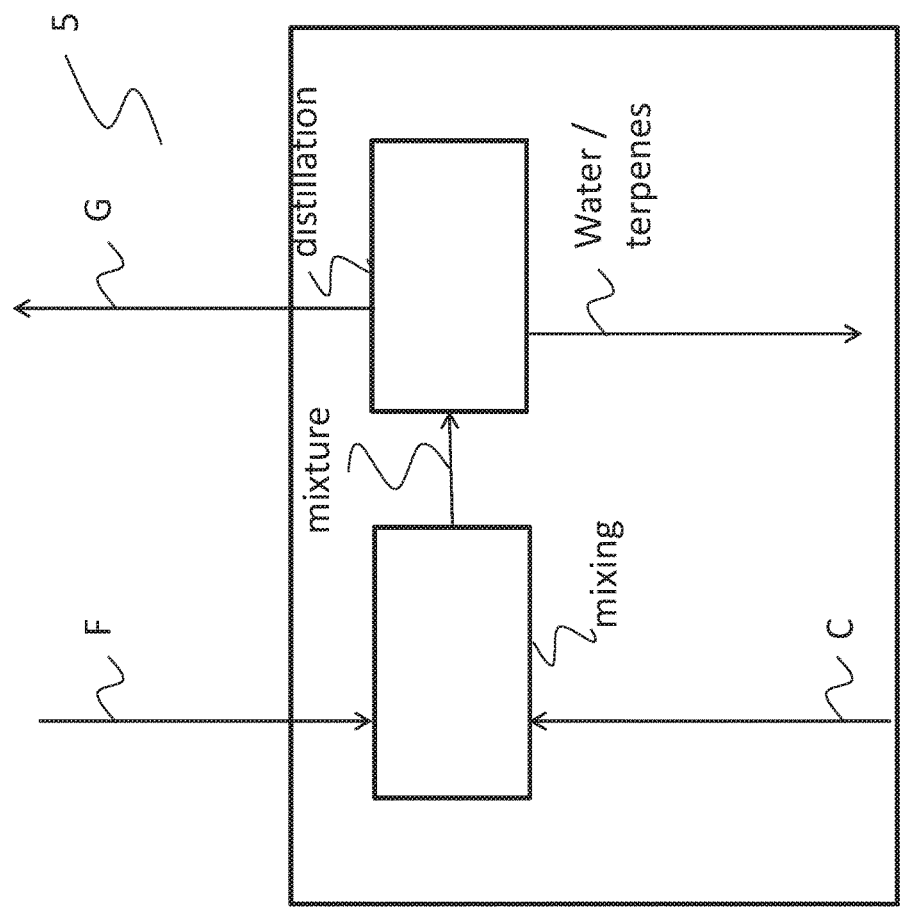
FIG. 4 shows a view of the internal elements of ACA Extraction Unit 5 of the FIGS. 1-3.

FIG. 3 shows a scheme according to another embodiment of the invention. Herein the acetylation fluid (b) recovered from wood acetylation is sent to the acetic acid/acetic anhydride separation unit (6) positioned downstream of the acetic anhydride production unit (4). The acetic acid/acetic anhydride separation unit (2) originally positioned downstream of the acetylation unit is dispensed with.

It will be understood that the schematic drawings serve to illustrate some parts of the equipments and production units as necessary to further illustrate some embodiments of the invention. The skilled person will be well aware of equipment parts and flow lines now shown, such as devices for providing heat, devices for providing pressure, vents for off-gas, and so on.

Where, in this description, it is spoken of "fluid communication", this refers to any connection between a first part or section of a plant and a second part or section of a plant via which fluids, including liquids and gases, can flow from the first part of the plant to the second part of the plant. In the event of liquids, such fluid communication is typically provided by piping systems, hoses, or other devices well-known to the skilled person for the transportation of fluids. In the event of gases, such fluid communication is typically provided by gas flow lines. Such gas flow lines typically comprise piping systems, or other devices well-known to the skilled person for the transportation of gases, if needed under pressures that are above atmospheric pressures or below (vacuum).

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein described units, such as a wood acetylation unit, a reactor unit or a distillation unit, comprise a plurality of such units positioned in parallel or in series.

Other variations to the disclosed embodiments can be understood and effected by those skilled in the art in practicing the claimed invention, from a study of the drawings, the disclosure, and the appended claims In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

The invention claimed is:

1. A process for the purification of acetic acid recovered from a wood acetylation process, wherein wood acetylation fluid comprising acetic acid and acetic anhydride obtained from a wood acetylation process is subjected to acetic acid recovery by distillation, and wherein acetic acid thereby recovered is mixed in a treatment section with a residual aqueous acetic acid stream from a unit for the production of ketene from acetic acid, and the resulting mixture is directly subjected to distillation so as to produce purified acetic acid.

2. A process according to claim 1, wherein the purified acetic acid is used as a reactant feed to the unit for the production of ketene.

3. A process according to claim 2, wherein produced ketene is subjected to reaction with acetic acid in a unit for the production of acetic anhydride, thereby producing acetic anhydride, said acetic anhydride being used as an acetylation fluid in said wood acetylation process.

4. A process according to claim 3, wherein the purified acetic acid is used as a reactant feed to the unit for the production of acetic anhydride.

5. A process according to claim 1, wherein produced ketene is subjected to reaction with acetic acid in a unit for the production of acetic anhydride, thereby producing acetic anhydride, said acetic anhydride being used as an acetylation fluid in said wood acetylation process.

6. A process according to claim 5, wherein the purified acetic acid is used as a reactant feed to the unit for the production of acetic anhydride.

7. A process according to claim 1, wherein the produced acetic anhydride is subjected to a concentration increase by distilling off acetic acid in a raw anhydride distillation unit, before being used in the wood acetylation process.

8. A process according to claim 7, wherein the acetic acid recovery from the wood acetylation fluid is conducted by distillation in the raw anhydride distillation unit.

9. A process according to claim 1, wherein the ketene produced in the unit for the production of ketene is fed as a reactant to the unit for the production of acetic anhydride.

10. A system comprising a wood acetylation section, a ketene production unit and a treatment section, wherein the treatment section is configured for the recovery of acetic acid from a residual aqueous acetic acid stream, the system comprising a separation section for the separation of acetic acid obtained from the wood acetylation unit, said separation section being in fluid communication with said treatment section, and wherein said treatment section comprises a distillation unit.

11. A system according to claim 10, wherein the ketene production unit is comprised in a section for the production of acetic anhydride, said section comprising the ketene production unit and, downstream thereof, an acetic anhydride production unit.

12. A system according to claim 10, which further comprises an acetic anhydride production unit.

13. A system according to claim 10, wherein the ketene production unit comprises a ketene furnace.

14. A system according to claim 13, wherein the ketene furnace has an outlet connected to a cooler, wherein the cooler is configured to separate produced ketene from residual aqueous acetic acid, and wherein the cooler has an outlet for produced ketene to the acetic anhydride production unit and an outlet for residual aqueous acetic acid to the distillation unit comprises in the treatment section.

15. A system according to claim 8, wherein the distillation unit of the treatment section is configured to also receive acetic acid from the separation section.

* * * * *